(12) United States Patent
Furrer

(10) Patent No.: US 9,500,571 B2
(45) Date of Patent: *Nov. 22, 2016

(54) HANDLING OF SAMPLE TUBES COMPRISING GEOMETRIC TUBE DATA

(71) Applicant: Roche Diagnostics Operations, Inc., Indianapolis, IN (US)

(72) Inventor: Frederic Furrer, Horw (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,790

(22) Filed: Aug. 19, 2015

(65) Prior Publication Data

US 2015/0355206 A1    Dec. 10, 2015

Related U.S. Application Data

(63) Continuation of application No. 14/159,898, filed on Jan. 21, 2014, now Pat. No. 9,140,632, which is a continuation of application No. 13/596,199, filed on Aug. 28, 2012, now Pat. No. 8,672,219.

(30) Foreign Application Priority Data

Sep. 29, 2011   (EP) .................................... 11183365

(51) Int. Cl.
*G06F 17/00* (2006.01)
*G01N 1/28* (2006.01)
*G01N 35/00* (2006.01)

(52) U.S. Cl.
CPC .......... *G01N 1/28* (2013.01); *G01N 35/00732* (2013.01); *G01N 2035/00821* (2013.01); *G01N 2035/00851* (2013.01)

(58) Field of Classification Search
CPC ......... G01N 2035/00495; G01N 2035/00504; G01N 2035/00524; G01N 2035/1025; G01N 35/02; G01N 35/10; G01N 35/00732; G01N 2035/00851; G01N 1/28; G01N 2035/00821; B01L 3/0275; B01L 3/5021; B01L 3/5082; B01L 3/50825; B01L 3/5085; B01L 3/50851; B01L 3/52
USPC ....................................................... 235/375
See application file for complete search history.

(56) References Cited

U.S. PATENT DOCUMENTS 5,137,260 A   8/1992  Pehr
5,631,165 A   5/1997  Chupp et al.
(Continued)

FOREIGN PATENT DOCUMENTS

CN   101126764 A   2/2008
JP   07-12969 U    3/1995
(Continued)

*Primary Examiner* — Thien M Le
(74) *Attorney, Agent, or Firm* — Roche Diagnostics Operations, Inc.

(57) ABSTRACT

A method for handling a sample tube containing a biological sample is presented. A tube label can be attached to the sample tube. The tube label can carry tube data. The tube data can comprise at least geometric tube data descriptive of at least one geometric property of the sample tube. At least the geometric tube data can be read from the tube label by a reader device. At least the geometric tube data from the reader device can be transmitted to a processing device. The processing device for handling the sample tube can be controlled in accordance with the at least one geometric property described by the read geometric data.

20 Claims, 3 Drawing Sheets

(56) References Cited

U.S. PATENT DOCUMENTS

| | | |
|---|---|---|
| 5,735,387 A | 4/1998 | Polaniec et al. |
| 5,819,508 A | 10/1998 | Kraft et al. |
| 6,586,255 B1 | 7/2003 | Hubert et al. |
| 6,599,476 B1 | 7/2003 | Watson et al. |
| 7,291,309 B2 | 11/2007 | Watson et al. |
| 7,435,387 B2 | 10/2008 | Itoh |
| 7,458,483 B2 | 12/2008 | Luoma, II |
| 7,922,073 B2 | 4/2011 | de la Huerga |
| 8,672,219 B2 * | 3/2014 | Furrer ............... G01N 35/00732 235/375 |
| 9,140,632 B2 * | 9/2015 | Furrer ............... G01N 35/00732 |
| 2002/0030302 A1 * | 3/2002 | Cleary ............... B44B 11/00 264/219 |
| 2003/0102367 A1 | 6/2003 | Monette et al. |
| 2005/0252973 A1 | 11/2005 | Itoh |
| 2006/0051239 A1 | 3/2006 | Massaro |
| 2006/0249582 A1 | 11/2006 | Golabek, Jr. et al. |
| 2009/0155571 A1 | 6/2009 | Mustonen |
| 2009/0208409 A1 * | 8/2009 | Summers ............ A61K 49/0466 424/1.21 |
| 2009/0324032 A1 | 12/2009 | Chen |
| 2010/0018330 A1 | 1/2010 | Marty et al. |
| 2010/0129789 A1 | 5/2010 | Self et al. |
| 2010/0300831 A1 | 12/2010 | Pedrazzini |
| 2011/0254665 A1 | 10/2011 | Lindsay et al. |
| 2012/0025985 A1 | 2/2012 | Bolander et al. |
| 2012/0138674 A1 | 6/2012 | Chen |
| 2012/0177535 A1 | 7/2012 | Fujita |
| 2012/0308435 A1 | 12/2012 | Fritchie |
| 2013/0130369 A1 | 5/2013 | Wilson et al. |
| 2015/0345688 A1 * | 12/2015 | Kersey ............... F16L 57/06 138/145 |
| 2015/0353817 A1 * | 12/2015 | Kersey ............... E21B 43/267 166/250.12 |

FOREIGN PATENT DOCUMENTS

| | | |
|---|---|---|
| JP | H09-43246 A | 2/1997 |
| JP | H09-211004 A | 8/1997 |
| JP | 10-115620 A | 5/1998 |
| JP | 2003-014770 A | 1/2003 |
| JP | 2009-204360 A | 9/2009 |
| TW | 201035553 A | 10/2010 |
| WO | 2009141957 A1 | 11/2009 |

* cited by examiner

HANDLING OF SAMPLE TUBES COMPRISING GEOMETRIC TUBE DATA

CROSS-REFERENCE TO RELATED APPLICATIONS

This application is a continuation of U.S. patent application Ser. No. 14/159,898, filed Jan. 21, 2014, now allowed, which is a continuation of U.S. patent application Ser. No. 13/596,199, filed on Aug. 28, 2012, now U.S. Pat. No. 8,672,219, which claims priority to EP 11183365.3, filed Sep. 29, 2011, all of which are hereby incorporated by reference.

BACKGROUND

The present disclosure generally relates to the field of in vitro diagnostics and, in particular, to a system and method for automatically handling biological samples.

Clinical laboratories face the challenge of having to process an increasing number of sample tubes per day while still having to guarantee that the analytical results derived from the samples are reproducible and correct. Errors may arise both in the pre-analytical, analytical and post-analytical stage of a potentially highly complex sample processing workflow. An additional challenge is the fact that a huge variety of different sample types exist which further complicate the handling and automated processing of the samples. In one aspect, the diversity of the sample tubes results from the diversity of sample processing workflows and tests which have meanwhile been developed for various diagnostic, analytical or other purposes.

In another aspect, the diversity results from different sample manufacturers using different materials, sample tube dimensions and cap color codes for collecting and processing different kinds of biological samples (e.g. blood, urine, serum or plasma samples) and/or for different kinds of analytical tests (coagulation tests, clinical chemistry tests, hematological tests, etc.). To meet the requirements in respect to analysis quality and cost effectiveness, intelligent solutions in the field of automated sample-handling devices are required.

Current pre- and post-analytical systems as well as analyzers require information on tube geometry, sample type, target volumes, cap type etc. in order to correctly handle and process sample tubes. In current systems, this information is gathered by cameras and/or sensors, or is defined by a user manually. Any manually executed step is, however, error prone and time consuming and therefore not suitable for implementing a high-quality sample processing workflow. Image analysis based approaches are often time consuming and may be error-prone. Errors may occur when frozen or very cold samples comprising ice or condensation water on their surface need to be processed. Ice and water may change the shape and optical parameters of a sample tube and may cause errors when an image is taken from such a sample for image analysis. Errors may also be caused by tubes sitting not vertically but diagonally in the rack, by a too weak light source being inadequate for letting the camera reliably detect the color of the tube or of the tube cap or may be caused by the tube protruding from the tube rack or by other error sources.

Therefore, there is a need to provide for an improved method and system for sample tube and sample tube handling.

SUMMARY

According to the present disclosure, a method for handling a sample tube containing a biological sample is presented. A tube label can be attached to the sample tube. The tube label can carry tube data. The tube data can comprise at least geometric tube data descriptive of at least one geometric property of the sample tube. At least the geometric tube data can be read from the tube label by a reader device. At least the geometric tube data from the reader device can be transmitted to a processing device. The processing device for handling the sample tube can be controlled in accordance with the at least one geometric property described by the read geometric data.

In accordance with one embodiment of the present disclosure, a system for processing sample tubes is also presented.

Accordingly, it is a feature of the embodiments of the present disclosure to provide for an improved method and system for sample tube and sample tube handling. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
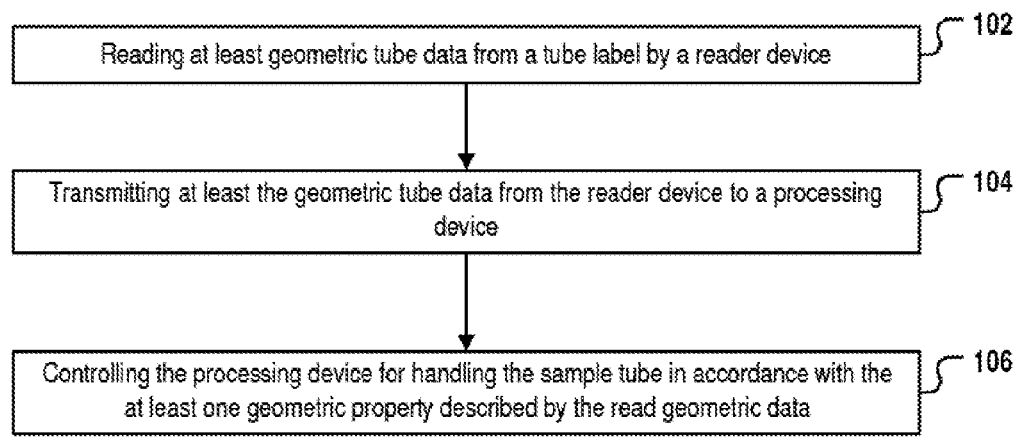
FIG. 1 illustrates a flowchart of a method for automatically handling a sample tube containing a biological sample according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A 'sample' or 'biological sample' can encompass any kind of tissue, or body fluid, derived from humans or any other organism. In one example, a biological sample can be a whole blood, serum, plasma, urine, cerebral spinal fluid, saliva sample or any derivatives thereof.

A 'sample tube', herein interchangeably referred to as 'tube', which can be either a sample collection test tube, also called 'primary tube', used to receive a sample such as a blood sample from a patient and to transport the sample contained therein to an analytical laboratory for diagnostic purposes, or a 'secondary tube', used to receive an aliquot of sample from a primary tube. A primary sample tube is typically made of glass or plastics, has a closed end and an open end, wherein the closed end can be closed by a cap. The cap may be of different materials, different shapes and color. The shape and/or color of the cap and/or the shape and/or color of the tube may be indicative of the type of the tube, the type of the biological sample contained therein and/or of the pre-analytical, analytical or post-analytical procedure to be executed on the sample. There are, for example, tubes containing an anticoagulant or a coagulation inducing agent, tubes containing gels facilitating the separation of plasma, etc. Different types of primary tubes are often just the result of customization by different primary tube manufacturers. For example, there are primary tubes of different diameters and/or different heights for receiving different amounts of samples. A 'secondary tube' is typically made of plastics and may have a lower degree of variation of size and type with respect to primary tubes. For example, secondary tubes may be smaller than primary tubes and may be designed to be closed with one type of similar types of closure, e.g. of the screw type.

The term 'cap' as used herein can encompass any type of closure comprising screw type caps and rubber stoppers, which can be opened and/or closed by a pulling/pushing and/or a screwing motion respectively.

A 'robotic unit' as used herein can be any kind of device, or device component that can automatically execute a sample workflow step on a sample tube.

The expression 'tube type' can refer to a category of sample tubes with a shared geometrical form, for example, the width, geometric shape, and/or height of the cap and/or the tube, etc. Commonly, but not necessarily, a shared geometrical form of a sample tube also corresponds to a shared type of sample to be carried by the sample tube type and/or corresponds to a shared type of analysis or pre- or post-analytical workflow step to be executed on the samples of the tube type. Different tube types typically are adapted for different pre-analytical, post-analytical or analytical requirements of a particular analysis or workflow step, e.g. a clinical chemistry analysis, a hematological analysis or a coagulation analysis. A mix up of sample tube types can make samples unusable for the scheduled analysis. To prevent errors in the collection and handling of samples, the sample caps of many tube manufacturers are encoded according to a fixed and uniform color scheme.

A 'processing device,' or 'workcell,' can be a standalone apparatus or a module within a larger instrument assisting users with sample processing. 'Sample processing' can comprise the detection, for example, quantitative and/or quantitative evaluation of samples for diagnostic purpose, and/or sorting and/or preparation of samples before detection, or storing and/or disposal of samples after detection. For example, a workcell can be related to analytical and/or pre-analytical and/or post-analytical sample processing steps, the steps being subsumed herein as 'in vitro' steps. Workcells may connect to each other and depend at least in part on each other, for example, each carrying out a dedicated task of a sample processing workflow, which may be a prerequisite before proceeding to the next workcell. Alternatively, workcells may work independently from each other, for example, each carrying out a separate task or a different type of analysis. A 'processing device' may be, for example, a capping unit, a de-capping unit, an aliquoter, a centrifuge or the like.

In one aspect, a method for handling a sample tube containing a biological sample is presented. A tube label is attached to the sample tube. The tube label carries tube data. Tube data can comprise at least geometric tube data descriptive of at least one geometric property of the sample tube. At least the geometric tube data is read from the tube label by a reader device. At least the geometric tube data is transmitted from the reader device to a processing device. The processing device for handling the sample tube is controlled in accordance with the at least one geometric property described by the read geometric data.

These features may be advantageous, because placing geometric tube data of a biological sample tube on the sample tube, it can be ensured that the geometric data is available throughout the whole sample processing workflow. In some systems using color encoded caps for identifying the sample tube type, information on the tube type may get lost when the sample tube is de-capped. Placing the geometric data on the sample tube can help ensure a fully automated processing of the sample and that uncapped tubes will not lose information on their geometric properties. Thus, the speed and cost-effectiveness of the sample handling workflow can be increased and the error proneness of the sample handling process can be reduced.

In other words, the geometrical data as the data being actually needed for a fully automated processing can be an inherent part of the tube and cannot be lost. According to further embodiments, a tube type identifier can be placed on the tube label in addition to the geometric data and/or can be derived in a second step from the geometric data read from the tube label. By deriving a tube type from the geometric data (and not, as in some systems, by deriving the geometric data from a detected tube type), it can also help guaranteed that the information on the tube type is not lost when a tube is, for example, decapped. As the tube type according to some of the embodiments can be a derivative of the geometric data and not vice versa, an extra level of security can be added to the system ensuring that the geometric data of a tube will always be available irrespective of its capping status.

In a further aspect, other embodiments may skip identifying a particular sample type first (for example, based on a color type or based on a tube type identifier printed on the sample tube) and gathering in a second step geometrical data for the identified sample tube type. By directly reading geometric properties from the tube label, the processing time required for gathering the geometrical data required by a sample handling unit can be reduced. In addition, the acquisition of the geometric data can be more error robust because the geometrical information is directly derived from the sample tube and not indirectly from an external storage having stored geometrical data in association with a sample type identifier. Thus, embodiments are not require to maintain a database with stored sample type identifiers corresponding to geometrical data or to maintain a connection to the database. Maintaining such a database is often not even possible as taking the sample and testing are done at different locations under the authority of different parties.

In a further aspect, embodiments can be much more flexible as they are able to dynamically determine the geometrical properties of a huge range of sample tubes. Thus, generic sample handling workcell components can be used which are not limited to sample tubes of a particular type or of a particular sample manufacturer. Thus, generic sample tube handling components can be combined with any kind of pre-analytic, analytic and post-analytic sample handling workcells or components thereof, because they can operate with any kind of sample tube type provided said sample tubes comprise a label specifying the geometric data of the sample tubes.

In a further aspect, embodiments can help guarantee that whenever a particular biological sample arrives at the input portion of a sample handling device, the geometric data required by the device for handling the sample can also be available. In some systems, the operation of complex automated sample workcells could be interrupted in case a sample of a wrong or unknown sample type was erroneously placed into the sample processing pipeline, because no geometrical data could be found for the sample of the unknown sample type. By using sample tubes with geometrical data on their labels, it can help ensure that all the information required to decide whether and how the sample tube should be handled by a particular sample handling device can always be available. Thus, bottlenecks in a processing workflow caused by an unidentified tube type can be avoided.

Disadvantages of camera-based systems, in particular, an inaccurate determination of a tube geometry, inaccurate determination of the volume of a sample due to unknown internal tube geometry, and an inaccurate determination of a spun or unspun tube state due to the opacity of the sample can be avoided. Camera based determination of a cap color for determining the tube type which again is used for determining the tube geometry has been turned out to be error prone and as soon as the cap is removed the tube type information is lost.

In a further aspect, updating a tube type library on a regular basis can made be unnecessary. If, for example, a tube manufacturer produces a completely new kind of tube whose geometric properties such as its diameter are stored or encoded in the tube label, a processing device does not have to be reprogrammed in order to "identify" the new tube type because the geometric data actually used for sample tube processing can be directly derived from the tube label. Thus, the processing device does not have to access a tube type library for retrieving geometric data stored in association with the identified sample type and accordingly there may not be a need to update such a tube type library on a regular basis. In summary, embodiments create and operate sample handling systems which can automatically determine the required geometric properties of any kind of tube type without having to maintain and query a tube type library. Provided the tube manufacturer, or another instance, has attached a tube label comprising geometric tube data encoded in a way enabling the reader device to interpret the data, any kind of new sample tube type can immediately and automatically be recognizable and processed by the sample handling system. It may not be required to update any sample tube type library with new tube types created by the tube manufacturer.

The term 'geometric tube data', as used herein, can encompass any data being descriptive of a geometric property of the whole tube or parts thereof, in particular data being descriptive of a geometric property of the tube shaft and/or tube cap or a combination thereof.

According to embodiments, the geometric property can be encoded in a bar code encoding standard such as, for example, PDF417, Codebloc or the like. This may be advantageous, because in case the tube type manufacturer and the sample processing device manufacturer use the same encoding/decoding standard, a workcell based on the encoding schema can be operable to process any kind of tube type. The only requirement can be that the tube's geometric properties are encoded in accordance with the standard (and that the tube dimensions lie within the physical possibilities of the processing device).

According to embodiments, the tube data can comprise one or more of the following geometric properties of the sample tube: outer tube diameter, inner tube diameter, false bottom location and shape, tube length, diameter of tube cap, and/or free height of tube cap.

The geometric properties can be provided in different ways. According to one embodiment, a geometric property can, for example, be provided in an incremental way. An upper or lower limit of a geometric property (i.e., the maximum or minimum value of the geometric property that a tube type can possibly have for being processed by the system, for example, inner tube diameter or tube length) can be known to a reader of a sample tube processing system which can read the geometric properties from a tube label. Alternatively, the limit can be known to a processing device, or computation unit, connected to the sample processing system and receiving tube data comprising the geometric properties from the reader.

'To be known' to a component as used herein implies that the data can be stored on a data storage being accessible and readable by the component. An increment of the geometric property can be encoded on the tube label. The value of the geometric property for the individual tube can then be determined by the reader, computation unit or processing device by adding (in case of a lower limit) or subtracting (in case of an upper limit) the increment to/from the limit.

In another embodiment, the value of geometric data can be stored on the tube label in the form of a numerical value. It can be possible that the numerical value does not have assigned a unit in the tube data and that the number can be interpreted after having been read by the reader as a value of a particular unit, e.g. millimeter. Likewise, the unit of the numerical value may be stored on the tube label as well.

The type of the geometric property can be encoded in the tube label. The type of the geometric property may, for example, be based on the position of a data value within the tube label and/or the position within a character sequence or data pattern contained on the tube label. For example, the first position in a sequence of numbers may comprise a value specifying the geometric property value type 'inner diameter', the second position may comprise a value specifying the geometric property type 'tube length' etc. Alternatively, the type of the geometric property can be provided on the tube label together with the value of the geometric property.

Table 1 shows an example for the above described coding schemes. Var2 is an incremental geometric property having assigned a minimum value and a maximum value for some geometry features. The tube label can carry the increment of the tube to which it is attached and the actual geometry can be determined by adding the increment to the Min value. In the shown example, the increment is 1 but it can be a multiple of 1 as well. Var3 provides the geometric parameters as plain numeric values and the reader can determine the type of geometric property which the numeric value represents due to the position of the numeric value in the sequence of numbers. In Var 4, an alphanumeric header can be provided in addition to the numeric value which describes the type of the geometric property whose value is indicated by the corresponding numerical value. Table 1 also depicts the number of Bits which can be needed to encode the respective information. For Var2, 21 Bits (3 Bytes) are needed while for Var3, 10 and for Var 4, 15 Bytes are needed on the label.

TABLE 1

| Feature | Unit | Min | Max | Increment | States | Var2 Bit | Var3 Numerics | Var4 Numerics | alpha header |
|---|---|---|---|---|---|---|---|---|---|
| Diameter | [mm] | 10 | 20 | 1 | 10 | 4 | 2 | 2 | 1 |
| Length | [mm] | 50 | 120 | 1 | 70 | 7 | 3 | 3 | 1 |
| False bottom | [mm] | 0 | 30 | 1 | 30 | 5 | 2 | 2 | 1 |
| Taper | degree | 0 | 5 | 1 | 5 | 3 | 2 | 2 | 1 |
| Cap type | — | 1 | 4 | 1 | 3 | 2 | 1 | 1 | 1 |
| | | | | | Sum | 21 | 10 | 10 | 5 |
| | | | | | Byte | 3 | | Sum Num. | 15 |

Table 2 shows the label size for a two dimensional barcode which is needed to encode the data of the above variants. In addition to the geometric data the space needed for a unique tube ID is also considered. It can be seen that the resulting label sizes fit well with the space available on sample tubes. Label of these sizes can be read by conventional two dimensional (2D) barcode readers even though when applied to cylindrical sample tube surfaces.

TABLE 2

| Topic | Unit | Var2 | Unit | Var 3 | Var 4 |
|---|---|---|---|---|---|
| ID | bytes | 4 | num. | 10 | 10 |
| Tube geo | bytes | 3 | num. | 10 | 15 |
| Total label size** | mm | 3.7 × 3.7 | mm | 3.7 × 3.7 | 4.1 × 4.1 |

According to some embodiments, the processing device can comprise a gripper having an opening position for receiving or releasing the sample tube or a cap of the sample and a gripping position for gripping the sample tube or a cap of the sample. At least the gripping position can be adjusted depending on the at least one geometric property. According to some embodiments, the gripper can be a tube gripper or a cap gripper. The system may also comprise any combination of one or more tube grippers, cap grippers or other forms of gripping devices controlled in dependence on geometrical data specified in the tube label. For example, the opening position may be a default position of a robotic gripper arm. According to some embodiments, both the opening and the gripping position can be adjusted depending on the geometric property. It may be advantageous to use an opening position whose gripping arm diameter is only slightly larger than the cap diameter of the tube in order to release the tube. Provided that the next sample tube processed has the same or a similar cap diameter like the previously processed tube, the gripping arm may be able to adjust its gripping diameter more quickly.

The term 'position' as used herein can be considered as any configuration, or state, of a robotic device or device component used to interact with and/or process a sample tube. A 'gripping position' can be a state, or configuration, allowing for the execution of the processing step while an 'opening position' can be a state or configuration allowing the release of the sample tube for further processing by other device components. The tube data may enable the gripper to automatically determine how and where to grip a tube and may enable a capper or de-capper to determine what caps are on a tube and to adjust the capping or de-capping mechanics accordingly.

According to some embodiments, the processing device can be a de-capper or a re-capper comprising a tube gripper and a cap gripper. The tube gripper can be controlled depending on the geometric property of the sample tube's shape and the cap gripper can be controlled in accordance with a geometric property of the tube cap.

According to some embodiments, the tube gripper can comprise a first tube gripping tool and a second tube gripping tool. The first tube gripping tool can be biased with respect to the second gripping tool and can cooperate with that second tube gripping tool such that the first tube gripping tool can grip and lift that tube, for example, from a conveyor belt, or rack, before the second gripping tool grips it. By such sequence, it can be achieved that the second gripping tool can grip with a force and a surface of contact which can be greater than the force and surface of contact of the first gripping tool respectively. This double gripping mechanism can enable gripping the sidewall of a tube in the often narrow space between a tube carrier and a closure with a smaller gripper and lifting it to a height wherein a larger and stronger gripping tool can grip a longer portion of the sidewall for a more secure grip.

According to some embodiments, the processing device can be an automated centrifuge comprising a loading station for loading sample tubes into the centrifuge. The loading station can comprise a gripper. The gripper can be controlled to place the sample tube into a centrifugation bucket depending on the read geometric tube data. This may be advantageous, because in several cases, similar or identical centrifugation programs may be applicable to multiple different biological samples contained in different tube types. Provided that the diameter and weight of the different sample tubes including their respective samples are approximately equal, loading them together into the same centrifuge based on shared geometrical tube data may increase the efficiency of sample handling workflows comprising centrifugation.

According to some embodiments, the geometric data can be used for determining the weight of the loaded samples. The determined weight again can be used for loading samples of approximately equal weight into centrifuge buckets lying oppositely to each other. In other words, the geometric data specified in tube labels of a plurality of sample tubes can be evaluated to distribute the sample tubes into buckets of a centrifuge automatically in a balanced way. Loading the centrifuge in a balanced way implies that the sample tubes inserted in opposing buckets of a centrifuge rotor are of largely equal weight, thus avoiding unbalancing the centrifuge. The weight can be, depending on the embodiment, be derived for example, by the geometric data specifying the inner dimensions of the tube in combination with a measured weight of the tube including its sample.

According to further embodiments, loading the centrifuge in a balanced way may be achieved even without assistance of a scale by determining, by the sensor or another optical reader device, the filling level of a sample in the sample tube and reading, by the reader device, at least geometrical data from the sample's tube label indicative of the geometric properties of the tube to allow for the calculation of the inner volume of the tube. The properties may be, for example, the tube diameter such as, for example, the inner tube diameter. The outer diameter may also allow for the calculation of the approximate inner tube volume. The determined filling level and the read geometric data indicative of the geometric properties can be used as input to calculate the actual volume of the sample contained in the sample tube. Assuming that the density of all samples is identical or approximately identical for all samples, samples of approximately equal volume can be treated as samples of approximately equal weight and can be loaded automatically into opposing buckets of the centrifuge rotor. In case samples of significantly different density are scheduled for collective centrifugation, in an additional step, the density can be taken as additional input parameter to calculate the weight of the samples from their respective volume and density and to load samples of approximately equal weight into opposing buckets of the centrifuge. The density information may, according to some embodiments, also be specified on the tube label. The features may be advantageous as they allow the loading of centrifuges in a balanced and fully automated way without the need for an additional device component (a scale) and without losing time for physical weighting.

According to some embodiments, the sample tube can have a screw cap. The tube data can comprise tube cap data indicative of the number of turns required to take the screw cap off the sample tube. The processing device can be a de-capper comprising a cap gripper. The cap gripper can be controlled to turn the screw cap the number of turns indicated by the read tube cap data.

According to some embodiments, the method can further comprise determining the approximate weight of the empty sample tube by using the read geometric properties or by reading the weight of the empty sample tube from the tube label by the reader device, weighing the sample tube containing the biological sample, and determining the weight difference between the empty sample tube and the sample tube containing the biological sample.

The determination of the approximate weight of the empty sample tube by using the read geometric properties may comprise calculating the volume of the glass or plastic material the sample tube is made of, for example, by using the inner and outer diameter of the sample tube as well as the tube height as input. Given the calculated volume and given the density of glass or the plastic, the weight of the tube can be calculated. According to other embodiments, the weight of the sample tube may be specified in the tube data. For example, a first weight information indicative of the weight of the empty sample tube can be read from the tube data. Then, the tube comprising the whole blood sample can be weighted and a second weight information can be obtained. The difference between the first and the second weight information can be indicative of the weight of the sample.

According to some embodiments, the method can further comprises determining the filling level of the sample tube by using the weight difference and the geometric properties of the sample tube. For example, from the known density of a particular sample type such as whole blood and from the determined sample weight, the volume of the whole blood sample, for example, in the unit "milliliter", can be calculated. By reading further geometric properties of the sample tube, such as, its inner diameter, the filling level of the sample tube can be calculated. This feature can be advantageous as it may be automatically and reliably determine the filling level even in case the sample tube surface is covered by water, ice or other substances hampering image-analysis based filling level determination. The determined filling level may allow a further sample processing unit to aliquot the sample without sucking in elements of a centrifugation pellet and without sucking in air by a pipet tip having been erroneously been positioned above the meniscus of the sample.

According to an embodiment, the reader can be an optical reader or an RFID reader.

According to an embodiment, the tube label can comprise an optically readable pattern, such as a barcode, such as, for example, a two-dimensional bar code.

A 'barcode' can be an optical machine-readable representation of data. A barcode can be, for example, a 1-dimensional (1D) or two-dimensional (2D) bar code. A linear barcode may comprise a set of parallel lines of varying width and spacings. A two-dimensional barcodes may comprise rectangles, polygons or other geometric patterns arranged in two dimensions. Data stored in barcodes can be read by optical reader devices also referred to as scanners.

Using a 2D barcode may be advantageous, because the information density, i.e., the amount of information per surface area of the sample tube, can allow for storing all of the information needed to process a particular sample tube type properly. For example, a 2D barcode specifying the exact height and wall thickness of a sample tube may drastically reduce the dead volume. In a further advantageous aspect, 2D barcodes can be particularly robust in respect to the gamma irradiation commonly used by tube manufacturers for sterilizing the manufactured and typically already packed sample tubes. According to some embodiments, a 5 mm×5 mm sized bar code can comprise all geometric data necessary for a de-capping or capping unit to automatically and correctly de-cap or re-cap the sample tube.

According to some embodiments, the 2D barcode can be a data matrix code. A data matrix code is a square 2D barcode comprising a plurality of square-shaped code elements scattered over the square area, wherein the scattering of the code elements can specify the data content of the data matrix code.

According to some embodiments, a scanner can read the optically readable pattern and transmits this pattern in the form of image data, for example, in a jpg or other image format, to an image analysis component. The transmission may be push- or pull based. The image analysis component may be part of the scanner (i.e., part of the reading device), part of the processing device or a part of a software component connected to the scanner and/or the processing system. The software component may be a middleware component of the laboratory, or a module of the laboratory information system (LIS) of the laboratory. The image analysis can evaluate this pattern for determining the geometric tube properties encoded therein.

According to some embodiments, an antenna can be attached to the sample tube. The tube label can comprise a sender for sending the tube data via the antenna.

According to some embodiments, the tube label can comprise an RFID circuit, such as, for example, a printed polymer electronic circuit. Using an RFID circuit may be advantageous because reading data from the chips is particularly robust against optically distorting effects such as ice or condensation water on the surface resulting from freezing a sample or from moving a frozen or cooled sample to a warm and humid environment. Using polymer electronic circuit may be particularly advantageous because such kind of circuits are robust against optically distorting effects and are also robust against damage caused by gamma irradiation applied during sterilization of the sample tubes.

According to some embodiments, the tube data can be printed or otherwise attached by the tube manufacturer on the sample tube after having accomplished the manufacturing process and before sterilization of the tubes.

According to some embodiments, the sample tube can be a false bottom tube and the tube geometric tube data, in addition, can comprise geometric properties of the false bottom, such as for example, the presence and/or position of the false bottom within the tube shaft. A false bottom can often be used for smaller liquid volumes when the outer tube shape is compatible with the regular processing tools. A processing unit pipetting liquid into such a false bottom tube or sucking liquid from the false bottom tube may need to automatically take the position of such a bottom into consideration to avoid perforating the bottom and for minimizing the dead volume. Thus, specifying the geometric properties of the false bottom tube may be advantageous as the data allows a fully automated and secure handling of false bottom tubes in addition to the 'conventional bottom tubes'. According to some embodiments, the reader device can evaluate the tube data for any specifications of geometric properties of a false bottom. In case the reader device, the controller or any other system component automatically determines the filling level from the geometric data, the geometric properties of the false bottom can be additional information for calculating the filling level in relation to the false bottom correctly.

According to some embodiments, the tube data can further comprise information on the presence, and optionally also on the position of a separator gel layer, on the cap design (Hemogard, Sarstedt, screw-cap, etc) and/or a tube type identifier.

According to further embodiments, the tube label in addition can comprise a pattern which changes upon application of a g-force over a minimum period of time and/or exceeding minimum g-force strength. Depending on the embodiment, an existing g-force sensitive pattern, for example, a further bar code section of the tube label, may be destroyed as the result of applying the g-force. Alternatively, a new pattern may become visible on a previously homogeneously colored tube label area upon applying the g-force, or a previously existing pattern in the area may be altered. Such a g-force sensitive tube label area is described, for example, in the EP patent application EP12818404 which is hereby included in its entirety by reference. The g-force sensitive pattern may likewise represent other forms of 2D codes, for example, matrix codes.

The features may be advantageous as camera based determination of the spun/unspun state of a sample tube tends to be error prone. By including a g-force sensitive label area in the tube label, static geometric properties of the tube can be combined with dynamically changing information on the tube state (spun/unspun) and both kinds of data can be made accessible to a reading device such as a bar code reader for a fully automated sample handling. This can avoid errors caused in a system when spun and unspun samples are pre-sorted manually or camera based. In a further advantageous aspect, systems already comprising an optical reading device such as a bar code scanner do not require any additional hardware component for determining the spun/unspun tube state.

According to some embodiments, a plurality of the sample tubes can be handled by the processing device. The at least one geometric property of each of the sample tube tubes can have any value within a predefined range irrespective of predefined sample tube types.

This may be advantageous, as several sample tube processing steps may solely depend on some geometric properties but not on a scheduled sample processing step (e.g. a particular analysis) or on the sample type. For example, a sample sorting unit may use the read geometric property of the samples to determine if the tube diameter or cap diameter of a particular sample tube lies within the range of tube diameters or cap diameters which can be processed by a particular capper or de-capper. Thus, all samples can be sorted into groups of samples in dependence of a range of diameters, whereby all samples within each group are processable by a particular capper or de-capper. Many cappers or de-cappers comprise a robotic gripper arm for capping and/or de-capping a sample tube and are characterized by a minimum and maximum possible gripper arm diameter. A sorting unit as described may be used to flexibly sort a plurality of sample tubes of different tube diameters or cap diameters in dependence on the requirements of the available cappers or de-cappers, thereby allowing a fully automated and at the same time highly flexible sample processing.

In a further aspect, a sample tube can have a tube label. The tube label can carry tube data. The tube data can comprise at least geometric tube data descriptive of at least one geometric property of the sample tube.

In a further aspect, a system for processing sample tubes is presented. The sample tubes can contain biological samples. At least one of the sample tubes can have a tube label attached to the sample tube that carries tube data. The tube data can comprise at least geometric tube data descriptive of at least one geometric property of the sample tube. The system can comprise a reader device for reading at least the geometric tube data from the tube label and a processing device for handling the sample tubes comprising a controller. The reader device can be coupled to the processing device for entering the geometric tube data into the controller. The controller can control the processing device depending on the geometric tube data.

According to some embodiments, the processing device can be a de-capper, a re-capper, a cap holder or an automated centrifuge.

According to some embodiments the system can further comprise sample tubes. Each of the sample tubes can have an attached tube label carrying tube data. The tube data of each sample tube can comprise at least the geometric tube data descriptive of at least one geometric property of the sample tube.

Referring initially to FIG. 1, flowchart is shown of a method for automatically handling a sample tube 212 containing a biological sample. In a first step 102, at least geometric tube data 210 can be read from a tube label by a reader device 202. The tube label can be attached to the sample tube. For example, the tube label may be an imprint having been printed on the surface of the sample tube during the manufacturing process. Likewise, the tube label may be attached to the surface of the sample tube after manufacturing, for example, by an adherent. The tube label can carry tube data comprising at least geometric tube data descriptive of at least one geometric property of the sample tube. In a further step 104, the geometric tube data read by the reader device can be transmitted from the reader device to a processing device 218. In step 106, the processing device can be controlled in accordance with at least one geometric property described in the read geometric data. For example, the controlling step may determine, based on the cap diameter specified in the read geometric data, which gripping position should be used by a robotic gripper 216 in order to de-cap the sample tube.

Figure 2:
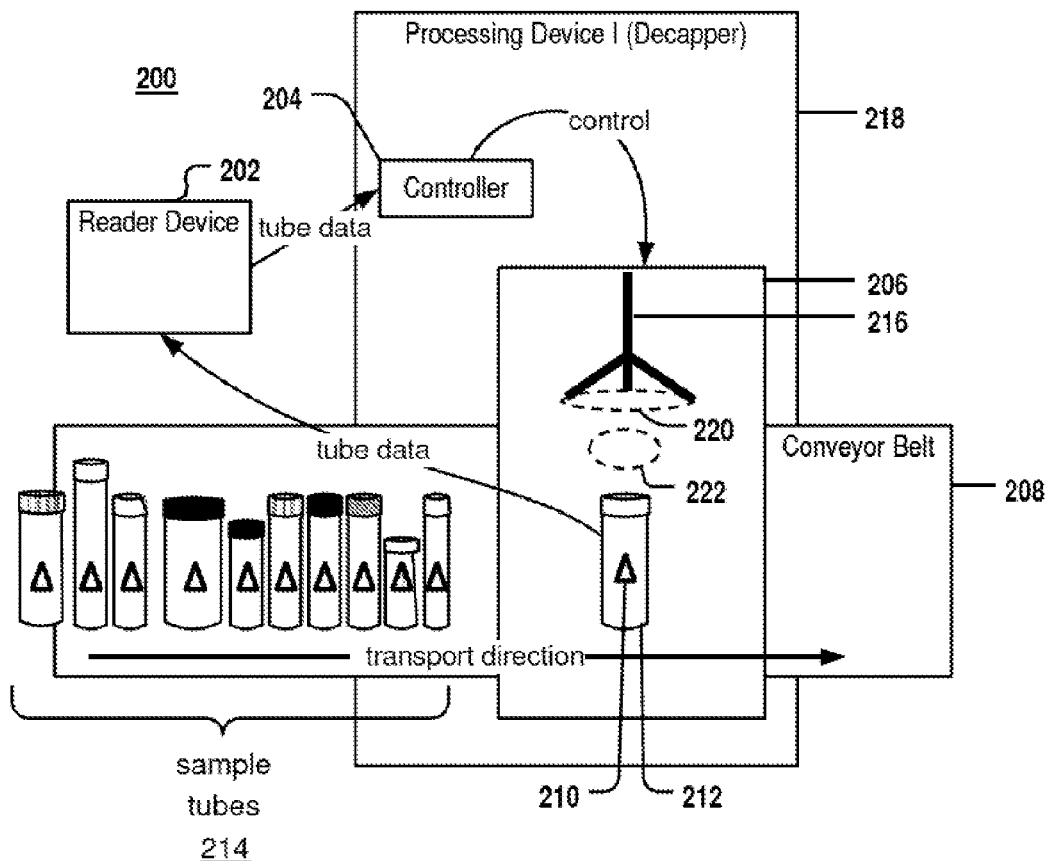
FIG. 2 illustrates schematically a system comprising a plurality of sample tubes, a reader device and a processing device according to an embodiment of the present disclosure.

FIG. 2 schematically depicts a system 200 for handling samples. The system can comprise a plurality of sample tubes 214, a reader device 202 and a processing device 218. The plurality of sample tubes of different tube types can comprise biological samples of different sample types. Sample tubes can be moved with respect to the processing device. In one exemplary embodiment, the sample tubes can be carried on tube carriers, which may be either single tube carriers, so-called "puks", or multi-tube carriers,—called "tube racks", which can comprise a plurality of tube receptacles for receiving, for example, up to five tubes or more and typically adapted to receive different types of tubes, i.e. of variable diameter and height. According to one embodiment, the processing system (de-capper) can comprise a tube conveyor belt for moving sample tubes on single tube carriers and/or tube racks (not shown). The conveyor belt may comprise a transportation unit, such as a transportation band or guide driven by a motor and arranged such that the tubes are moved stepwise to bring one tube at a time in alignment with the de-capping station. The transportation unit may however move tubes on special carriers and vice versa may be customized according to the requirements of a processing device. In some embodiments (not shown), a reformatting device for transferring sample tubes for puks and/or tube racks to these special carriers may be coupled to the processing device.

The plurality of samples arrives at an input position of the system and can be transported by the conveyor belt 208 to a 'reading position' where the label of each of the samples can be read by a reader device 202. The reader device 202 can read at least geometric tube data indicated in the tube label and can forward the read tube data to a controller 204 as part of a processing device 218. According to one embodiment, the reader device may be a scanner that reads optical data such as, for example, a 2D code, from the tube label 210 of the sample tube 212. According to another embodiment, the reader device 202 may be an RFID reader that reads data from an RFID circuit 308.2 that is part of the label 210 of the sample tube. The processing device 218 can comprise a robotic unit 216 for executing a workflow step on the sample tube 212. Depending on the embodiment, the processing device 218 may be a unit of a pre-analytical, analytical, or post-analytical sample handling system or a complete pre-analytical, analytical or post-analytical workcell. The robotic unit may be a gripper controlled by the controller 204 that depends on the tube data being received by the controller from the reader device 202. The gripper may be part of a gripper unit.

According to one embodiment, the processing device can be a de-capper that automatically de-caps the loaded sample tubes. For example, the gripper 216 can decap a plurality of different tubes having caps of differing diameters, cap heights, surface textures and the like.

According to one embodiment, the gripper can be a robotic arm and comprises an opening position 220 for receiving and/or releasing a sample tube and a gripping position 222 for gripping the sample tube. At least the gripping position is adjusted depending on the at least one geometric property of the sample tube.

According to some embodiments, the gripper 216 can be a robotic gripper arm that dynamically adjusts the diameter of the gripper arm to the diameter of the tube cap specified in the received tube data. The gripper arm may have a particular default diameter in its 'opening position' and may increase or diminish the diameter until the cap diameter of the sample tube is reached provided that the diameter does not exceed physically the given maximum or minimum diameter of the gripper 216. By adjusting the gripper arm diameter to the read cap diameter, the gripper 216 can process each of a plurality of different sample tubes 214 having different cap diameters. Depending on the embodiment, the gripper can dynamically adjust its vertical and/or horizontal position within the gripper unit 206 dynamically in dependence on the geometric data of the sample tube and thus can dynamically adjust to different tube heights, tube cap heights, cap textures (smoothed, grooved, etc.), cap shapes (round, polygonal) etc.

According to some embodiments wherein the tube label comprises information on the number of turns required to cap or decap a sample tube, the gripper 216 may use this information for executing the de-capping step by applying the number of turns specified in the geometric tube data of the tube label to the tube's cap.

Figure 3A:
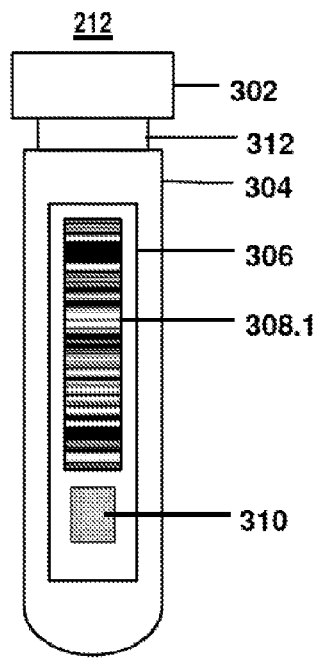
FIG. 3a illustrates a sample tube comprising a barcode label according to an embodiment of the present disclosure.

FIG. 3*a* depicts a sample tube 212 comprising a tube label 306 with a barcode 308.1. The sample tube can comprise a cap 302 which may be, for example, a press-lock or a screw cap. The label 306 may comprise a human readable label section in addition to the barcode 308.1. The tube label 306 may be an imprint on or may be attached to the surface 304 of the sample tube. The barcode can be a 2D code which can be read by an optical reader device such as a scanner. The tube shaft of the depicted sample tube can comprise a tube neck 312 which may be absent in other tube types.

Figure 3B:
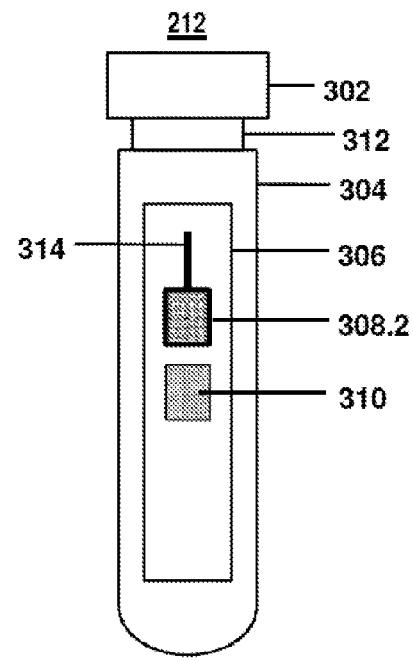
FIG. 3b illustrates a sample tube comprising an RFID circuit according to an embodiment of the present disclosure.

FIG. 3*b* depicts a sample tube 212 corresponding to the sample tube of FIG. 3*a* but comprising an RFID circuit 308.2 instead of a barcode as tube label. In one embodiment, the RFID circuit 308.2 can be a passive RFID circuit receiving its energy via the antenna 314 attached to the sample tube and to the RFIC circuit. The corresponding reading device can be a RFID reader. The RFID reader or another device can generate an electromagnetic field acting as energy source for the RFID circuit. When the RFID circuit is moved into the electromagnetic field, the RFID circuit can derive, via its antenna 314, enough energy to send the tube data stored on the RFID circuit via the antenna to the RFID reader device.

Figure 4:
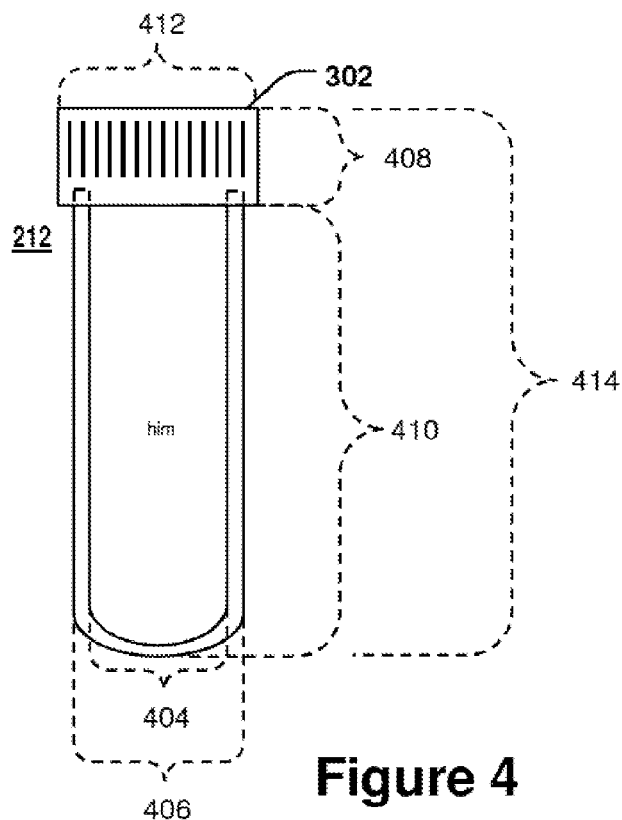
FIG. 4 illustrates various parts of a sample tube according to an embodiment of the present disclosure.

FIG. 4 depicts various parts of a sample tube. The sample tube can have an inner tube diameter 404 and an outer tube diameter 406. The height of a tube cap as visible from the outside of the tube (which may cover some parts of the tube shaft) is referred to as free height of the tube cap 408. A cap may not be present in every tube type, but every tube comprises a tube shaft of a particular tube shaft length. The length distance from the bottom of the tube to the top of the tube cap (or the top of the tube shaft in case of tubes lacking a cap) is referred herein as tube length 414. The tube shaft length 410 of a tube lacking a cap is identical to its tube length. The outside diameter of the tube cap as seen from a bird's eye perspective is referred to as 'diameter of the tube cap' 412.

Figure 5:
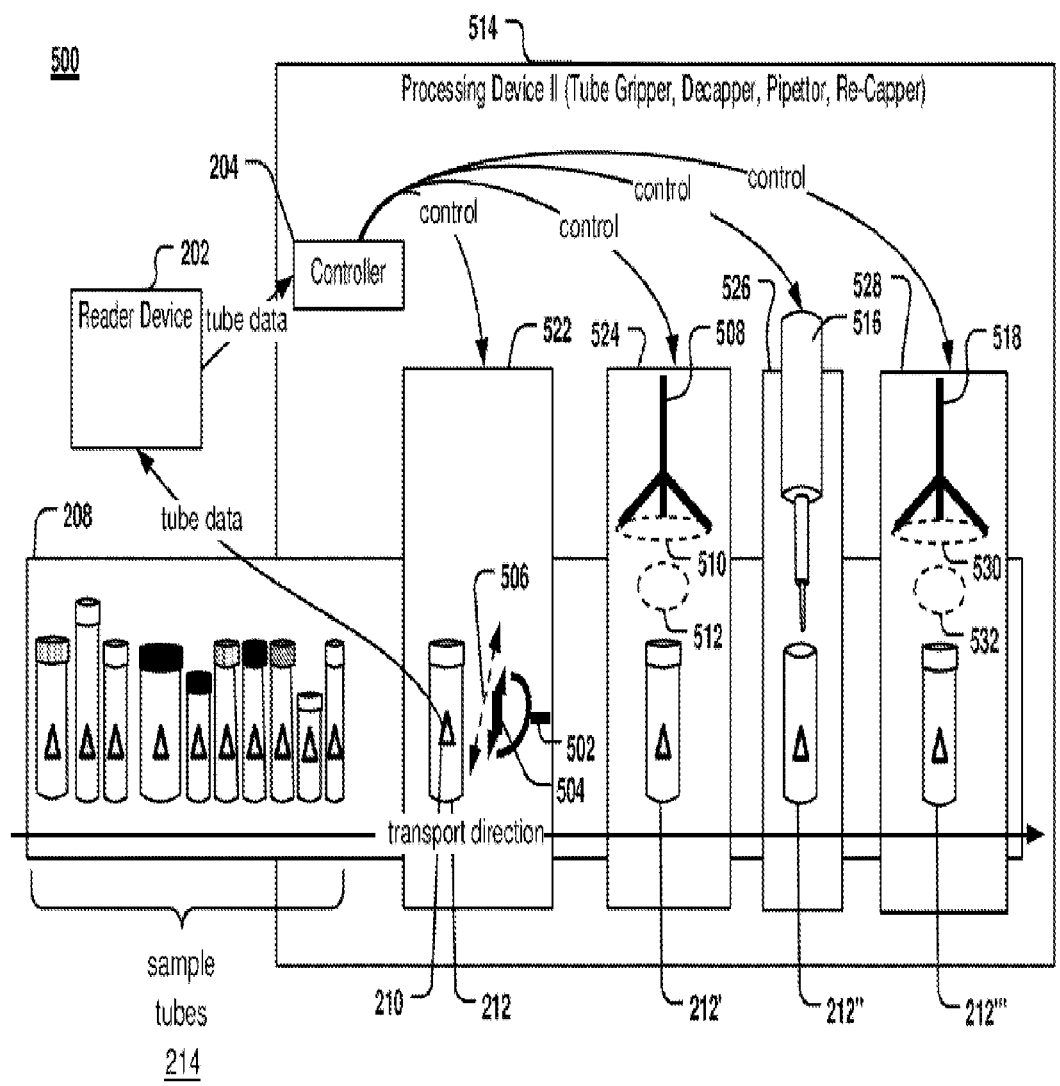
FIG. 5 illustrates schematically a system comprising a plurality of sample tubes, a reader device and another processing device according to an embodiment of the present disclosure.

FIG. 5 schematically depicts a further system 500 for automated sample handling. The system can comprise a plurality of sample tubes 214, a reader device 202 and another processing device 514. The processing device can comprise a tube gripping unit 522 with a tube gripper 502, a decapping unit 524 with a tube cap gripper 508, a pipetting unit with a pipettor 516 and a re-capping unit 528 with a re-caper 518. The processing device 514 can be a fully automated sample workcell that transports a plurality of samples 214 via a conveyor belt 208 or other robotic transportation facility. The tube gripper 502 can be a robotic arm controlled in dependence on the geometric property of the sample tube's shape, for example, the outer tube diameter or the tube height, but not the geometric properties of the tube's cap (if any). The controller may specify the position of the gripping arms of the tube gripper in accordance with geometric tube data received from the reader device 202. Two different positions of the gripper arms, an opening position 506 and a gripping position 504, can be indicated by two dotted arrows. The cap gripper 508 of the de-capping unit 522 and also the cap gripper 518 of the re-capping unit 528 respectively can be robotic arms controlled in dependence on the geometric property of the sample tube's cap, for example, the cap diameter or the free height of the tube cap. Some geometric properties of the tube, such as, for example, its height, may also be used by the cap grippers to dynamically adjust the vertical position of the cap grippers to the tube cap height According to some embodiments, the tube gripper 502 can position the tube for enabling the cap gripper 508 to de-cap the positioned sample tube. Once the cap has been successfully removed from the sample tube, the pipettor 516 may suck aliquots from the sample or pipet a reagent into the sample. According to some embodiments, the controller 204 can use at least some of the geometric data read from the sample tube label 210 to calculate the volume that can be sucked from or added to the sample tube 212" without touching the tube bottom and without overloading the sample tube with liquid. The sample tube can then be automatically forwarded from the pipetting unit 526 to a re-capping unit 528 wherein a cap gripper 518 having different gripping diameters 530, 532 can add a new cap onto the sample tube 212". The final sample tube 212''' may be transported by the conveyor belt to a storage unit (not shown). The various sample processing units 522, 524, 526 and 528 may be part of the same or of multiple different hardware modules or lab-devices.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A system for processing sample tubes, the sample tubes containing biological samples, each of the sample tubes having a tube label attached, the tube label carrying tube data, the tube data comprising at least geometric tube data being descriptive of at least one internal geometric property of the sample tube, the system comprising:
   a reader device for reading and transmitting the at least the geometric tube data from the tube labels;
   a processing device for handling the sample tubes; and
   a controller for receiving the transmitted geometric tube data from the reader device and controlling the processing device based on the transmitted geometric data.

2. The system according to claim 1, further comprising, a sample sorting unit in communication with the controller, wherein the sample sorting unit sorts the sample tubes into groups based on a shared geometric property within a predefined range before proceeding to the processing device.

3. The system according to claim 2, wherein the predefined range determines the processing device to be used.

4. The system according to claim 2, wherein the predefined range is a range of sample tube diameters.

5. The system according to claim 2, wherein the predefined range is a range of sample tube cap diameters.

6. The system according to claim 2, wherein the processing device is a capper or decapper.

7. The system according to claim 6, wherein the predefined range for each capper or decapper is a minimum and maximum possible gripper arm diameter for that capper or decapper.

8. The system according to claim 1, wherein the at least one internal geometric property of the sample tube comprises at least one of an inner tube diameter, a location of a false bottom, and a shape of a false bottom.

9. The system according to claim 1, wherein the geometric tube data comprises outer sample tube diameter, inner sample tube diameter, false bottom location, false bottom shape and sample tube length.

10. The system according to claim 1, wherein the type of sample tube being processed is derived from the geometric tube data.

11. The system according to claim 1, wherein the controller adjusts the amount of biological sample collected from the sample tube based on the transmitted geometric data.

12. The system according to claim 1, wherein the systems comprises more than one processing device.

13. A method for handling sample tubes containing biological sample, a tube label being attached to each of the sample tubes, the tube labels carrying tube data, the tube data comprising at least geometric tube data being descriptive of at least one internal geometric property of each of the sample tubes, the method comprising:
   reading at least the geometric tube data from the tubes label by a reader device;
   transmitting at least the geometric tube data from the reader device to a controller; and
   controlling a processing device for handling the sample tubes in accordance with the at least one internal geometric property described by the read geometric data from the controller.

14. The method according to claim 13, further comprising,
   sorting the sample tubes based on a shared geometric property within a predefined range before the sample tubes are handled by the processing device.

15. The method according to claim 14, wherein the predefined range determines which processing device handles the sample tubes.

16. The method according to claim 14, wherein the processing device caps or recaps the sample tubes.

17. The method according to claim 16, wherein the processing device caps or recaps the sample tubes with a robotic arm.

18. The method according to claim 17, wherein the robotic arm has a minimum and maximum gripper arm diameter.

19. The method of claim 18, wherein the minimum and maximum gripper arm diameter defines the predefined range.

20. The method according to claim 13, further comprising,
   adjusting the amount of biological sample collected from the sample tube based on the read geometric data.

* * * * *